(12) United States Patent
Jones et al.

(10) Patent No.: US 6,358,535 B1
(45) Date of Patent: Mar. 19, 2002

(54) METHOD OF TREATING HERNIATED DISKS

(76) Inventors: Bobby R Jones; Patricia L Jones, both of P.O. Box 877610, Wasilla, AK (US) 99687

( * ) Notice: Subject to any disclaimer, the term of this patent is extended or adjusted under 35 U.S.C. 154(b) by 23 days.

(21) Appl. No.: 09/714,755

(22) Filed: Nov. 16, 2000

Related U.S. Application Data

(60) Provisional application No. 60/159,526, filed on Nov. 16, 1999.

(51) Int. Cl.[7] .............................................. A61K 31/59
(52) U.S. Cl. ......................... 424/555; 424/523; 424/554
(58) Field of Search ................................ 424/523, 554, 424/555

(56) References Cited

U.S. PATENT DOCUMENTS 5,554,361 A * 9/1996 Dixon

FOREIGN PATENT DOCUMENTS

DK     WO 200032210    * 12/1998

* cited by examiner

*Primary Examiner*—Christopher R. Tate
*Assistant Examiner*—Randall Winston
(74) *Attorney, Agent, or Firm*—Michael J. Tavella

(57) ABSTRACT

A method of treating herniated discs that involves taking a daily dose of cod liver oil orally. The cod liver oil acts to lubricate the tissues and reduces inflammation and swelling. Pain relief is experienced within three to four weeks after the start of the treatment. Once pain relief is reached, the treatment continues. If the cod liver oil treatment is stopped, the inflammation and pain reappear.

2 Claims, No Drawings

METHOD OF TREATING HERNIATED DISKS

CROSS REFERENCE TO RELATED APPLICATIONS

This application claims priority based on U.S. Provisional Application No. 60/159,526 filed Nov. 16, 1999.

STATEMENT REGARDING FEDERALLY SPONSORED RESEARCH AND DEVELOPMENT

Not Applicable

BACKGROUND OF THE INVENTION

1. Field of the Invention

This invention pertains to methods of treating herniated disks and particularly to treating herniated disks with cod liver oil.

2. Description of Related Art

Herniated disks are a condition caused by either a swelling or rupture of the disk pads between the vertebrae, which causes the disk material to press against the spinal nerves. This condition can cause pain, numbness or loss of function of the limbs. Currently, treatment of this condition involves either surgery or a treatment involving injections of enzymes that dissolve the swollen tissue. Both of these options are costly and painful.

DETAILED DESCRIPTION OF THE INVENTION

My method overcomes these difficulties. It simply involves taking a daily dose of cod liver oil orally. The cod liver oil acts to lubricate the tissues and reduces inflammation and swelling. Pain relief is experienced within a three to four weeks of the start of the treatment. Once pain relief is reached, the treatment continues. If the cod liver oil treatment is stopped, the inflammation and pain reappear.

In the preferred embodiment, the cod liver oil is taken orally in a dose of between about 1 to 5 milliliters per day.

The present disclosure should not be construed in any limited sense other than that limited by the scope of the claims having regard to the teachings herein and the prior art being apparent with the preferred form of the invention disclosed herein and which reveals details of structure of a preferred form necessary for a better understanding of the invention and may be subject to change by skilled persons within the scope of the invention without departing from the concept thereof.

We claim:

1. A method of treatment for the relief of herniated disk pain comprising the step of: orally ingesting an effective quantity of cod liver oil to a subject in need thereof to relieve the herniated disk pain.

2. The treatment of claim 1 wherein the quantity of cod liver oil is between about 1 to 5 milliliters per day.

* * * * *